United States Patent [19]

Gorton et al.

[11] 4,002,695

[45] Jan. 11, 1977

[54] PROCESS FOR MAKING TETRACHLOROETHYLENE

[75] Inventors: Earl M. Gorton; Robert E. McGreevy, both of Sulphur, La.

[73] Assignee: PPG Industries, Inc., Pittsburgh, Pa.

[22] Filed: Feb. 6, 1976

[21] Appl. No.: 655,930

[52] U.S. Cl. .......................................... 260/654 D
[51] Int. Cl.² ........................................ C07C 21/00
[58] Field of Search ................................ 260/654 D

[56] References Cited

FOREIGN PATENTS OR APPLICATIONS 201,386  10/1967  U.S.S.R. .................. 260/654 R

*Primary Examiner*—D. Horwitz
*Assistant Examiner*—Joseph A. Boska
*Attorney, Agent, or Firm*—Roger S. Benjamin

[57] ABSTRACT

Tetrachloroethylene is obtained by the vapor phase reaction of carbon tetrachloride in the presence of elemental hydrogen and a barium chloride catalyst at a temperature of at least 500° C.

3 Claims, No Drawings

PROCESS FOR MAKING TETRACHLOROETHYLENE

BACKGROUND OF THE INVENTION

Tetrachloroethylene may be prepared by pyrolysis of carbon tetrachloride. Reaction temperatures for pyrolysis of carbon tetrachloride are variously reported as being of the order of 800° C. (See, U.S. Pat. No. 3,364,272 issued to J. W. Ager, Jr.), as temperatures at the high end of the temperature range 600° C.–1500° C. (U.S. Pat. No. 1,930,350 issued to C. J. Strosacker et al), and as temperatures within the range of 1300° C.–1400° C. (U.S. Pat. No. 2,447,410 to Hampel).

The use of prior art high pyrolysis temperatures generally necessitates high energy input, limited selection of reactor construction materials, and more extensive separation of unwanted by-products.

It is also known to hydrogenate chloro-carbon and chloro-hydrocarbon compounds to compounds having the same number of carbon atoms by the use of elemental hydrogen and copper catalysts at temperatures of 350° C.–550° C. (See, U.S. Pat. No. 2,886,605 issued to H. H. McClure et al).

THE INVENTION

The invention is a process for preparing tetrachloroethylene. The process is performed by pyrolyzing carbon tetrachloride vapor with a barium chloride catalyst in the presence of hydrogen at a temperature of at least 500° C.

The carbon tetrachloride reactant may be supplied to the reaction zone as a pure compound or as part of a mixed reaction stream containing other chlorinated organic compounds such as chloroform or hexachloroethane. It is preferred to use a chloro-organic feed which has a carbon tetrachloride concentration of at least 50 weight percent to assure predominant formation of desired tetrachloroethylene product.

The catalyst used in the process of this invention is barium chloride. The catalyst is solid at the temperature of reaction and may be employed directly in its solid form. Preferably, the barium chloride catalyst is placed on a conventional catalyst support such as diatomaceous earth, clays, or activated carbon. The use of a support makes the catalyst less subject to mechanical stress and increases its effective surface area. An illustrative method of catalyst preparation is to treat activated carbon with an aqueous solution of barium chloride, and vaporize the retained water until the weight of barium chloride the over one percent of the combined dry weight of barium chloride and activated carbon support. The ratio of catalyst (barium chloride plus support) to carbon tetrachloride feed is not critical, but to assure adequate contact of the feed with the catalyst in the reaction zone without undue residence time of the feed being required, a catalyst content representing at least 0.1 volume percent of the reaction zone is preferably employed. The rate of feeding carbon tetrachloride to the reaction zone is not critical, however, it is preferred to transfer the vaporized feed through the reaction zone at a rate of 0.05 grams per liter of reaction zone per minute or higher.

The pressure at which the reaction is performed is not critical. Subatmospheric or superatmospheric pressures may be employed. However, it is generally advantageous to employ autogenous pressures for reasons for convenient operation.

The reaction temperature must be at least about 500° C. It is especially preferred to operate the process of this invention at temperatures between 525° C. to 700° C. Higher reaction temperatures (above 775° C.) are not preferred because they encourage side reactions (e.g., formation of $Cl_2$) and represent an additional cost and inconvenience in process operation.

The hydrogen supplied to the reactor is element hydrogen. Hydrogen may be present with the carbon tetrachloride vapor in the reaction zone in a proportion which is more or less than the stoichiometric amount necessary to form tetrachloroethylene by the chemical equation: $2 CCl_4 + 2H_2 \rightarrow CCl_2=CCl_2 + 4 HCl$. However, to assure the maximum extent of reaction it is preferable to have hydrogen present in at least stoichiometric proportions, namely, at least one mole of hydrogen present for each mole of carbon tetrachloride.

If desired, inert diluents such as nitrogen or noble gases may be present in the feed stream or the reaction zone. It is desirable to exclude reactive materials such as water (forms hydrochloric acid) and oxygen (encourages formation of by-products).

The reactor may be of any conventional shape having an inlet and outlet and means for heating (the reaction is endothermic). Materials used for reactor construction are those known to have the chemical resistance necessary to retain the feed and organic products at the prescribed reaction temperatures. Suitable reactor materials include refractories such as quartz and zirconium oxide.

The catalyst may be contacted with the carbon tetrachloride feed and hydrogen in the reaction zone in any convenient manner but it is preferred to have the catalyst contained in the reaction zone in a convenient form such as a fixed bed or a fluidized bed. The reactants (carbon tetrachloride vapor and hydrogen) may be supplied to the reaction zone either separately or premixed.

The organic product output of the reactor may be purified by known fractionation methods such as stripping and rectification to give tetrachloroethylene, miscellaneous by-products, and unreacted carbon tetrachloride. The unreacted carbon tetrachloride may be recycled to the reaction zone together with fresh carbon tetrachloride containing feed to provide continuous process operation.

The invention may be understood in more detail from the following illustrative examples. It should be understood that these examples are not to be construed as limiting the invention.

EXAMPLE I

A 1 inch (2.54 centimeters) diameter, 30 inch long (76 centimeters) zirconia tube was wrapped with electrical heating elements. Eighteen and one-half inches (18 –½) (46 centimeters) of the bottom section of the tube were charged with barium chloride catalyst composition to form a fixed bed of catalyst particles. The reaction tube was vertically supported and vaporized dry carbon tetrachloride feed introduced at its lower end at a rate of 2 grams per minute for a period of one hour. Dry hydrogen gas was premixed with the varporized carbon tetrachloride feed stream in a ratio of 0.8 moles of hydrogen to 1.0 moles of carbon tetrachloride. The temperature range of the reaction zone was maintained as a graduated temperature zone ranging from 537° C. to 649° C.

The barium chloride catalyst composition was prepared by adding a concentrated aqueous barium chloride solution to granulated (100 mesh) activated carbon and evaporating the retained water. This resulted in a catalyst having 20 percent barium chloride base on the combined dry weight of activated carbon and barium chloride.

An analysis of reactor output is given in Table 1 below:

TABLE 1

| | |
|---|---|
| Organic Product Output | 82.9 grams per hour |
| HCl output | 19.5 grams per hour |
| $Cl_2$ output | 7.3 grams per hour |
| Analysis of Organic Product (100 weight percent basis) | |
| Carbon Tetrachloride | 57.13 weight percent |
| Tetrachloroethylene | 37.94 weight percent |
| Hexachloroethane | 2.63 weight percent |
| Hexachlorobutadiene | 0.65 weight percent |
| Hexachlorobenzene | 1.54 weight percent |
| Other | Balance |

EXAMPLE II

The experimental procedure and reaction conditions of Example I were duplicated except that no hydrogen gas was mixed with the carbon tectrachloride feed or otherwise sent to the reaction zone. An analysis of reactor output is given in Table 2 below:

TABLE 2

| | |
|---|---|
| Organic Product Output | 116.1 grams per hour |
| $Cl_2$ output | 9.98 grams per hour |
| Analysis of Organic Product (100 weight percent basis) | |
| Carbon Tetrachloride | 74.16 weight percent |
| Tetrachloroethylene | 13.53 weight percent |
| Hexachloroethane | 12.09 weight percent |
| Hexachlorobutadiene | 0.02 weight percent |
| Other | Balance |

Operation according to the process of this invention results in a high proportion of tetrachloroethylene and a correspondingly small proportion of by-products such as hexachloroethane.

Although the present invention has been described with reference to the specific details of particular embodiments thereof, it is not intended to limit the scope of the invention, except insofar as the specific details are recited in the appended claims.

We claim:

1. A method of making tetrachloroethylene which comprises contacting a reaction mixture of carbon tetrachloride vapor and elemental hydrogen with a barium chloride catalyst at a temperature of at least 500° C. and thereafter recovering tetrachloroethylene from the reaction product.

2. The method of claim 1 wherein hydrogen is present to the extent of at least one-half mole per mole of carbon tetrachloride.

3. The method of claim 1 wherein the reaction mixture is contacted with the catalyst at a temperature between 525° C. to 700° C.

* * * * *